(12) United States Patent
Yamada et al.

(10) Patent No.: US 7,378,546 B2
(45) Date of Patent: May 27, 2008

(54) METHOD FOR PRODUCING 2-AMINO-5-IODOBENZOIC ACID

(75) Inventors: Kazuhiro Yamada, Aichi (JP); Norio Fushimi, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/573,583

(22) PCT Filed: Aug. 3, 2005

(86) PCT No.: PCT/JP2005/014212

§ 371 (c)(1),
(2), (4) Date: Feb. 12, 2007

(87) PCT Pub. No.: WO2006/016510

PCT Pub. Date: Feb. 16, 2006

(65) Prior Publication Data

US 2007/0219396 A1    Sep. 20, 2007

(30) Foreign Application Priority Data

Aug. 10, 2004  (JP) .............................. 2004-233711

(51) Int. Cl.
*C07C 229/00* (2006.01)

(52) U.S. Cl. ....................................................... 562/456

(58) Field of Classification Search ...................... None
See application file for complete search history.

(56) References Cited

U.S. PATENT DOCUMENTS 3,991,105 A    11/1976  Wille
5,523,472 A    6/1996   Rohrscheid et al.

FOREIGN PATENT DOCUMENTS

| EP | 0130224 | 1/1985 |
|---|---|---|
| JP | 05-058974 | 3/1993 |
| JP | 2004-043474 | 2/2004 |

OTHER PUBLICATIONS

Klemme et al, Journal of Organic Chemistry, Synthesis of Iodohippuric Acids, I. 2,5-, 3,5- and 3,4-Diiohippuric Acids, 1940, 5, pp. 227-234.*

* cited by examiner

*Primary Examiner*—Paul A. Zucker
(74) *Attorney, Agent, or Firm*—Antonelli, Terry, Stout & Kraus, LLP.

(57) ABSTRACT

A method for producing 2-amino-5-iodobenzoic acid which comprises bringing 2-aminobenzoic acid (A) and molecular iodine (B) into reaction with each other in the liquid phase in the presence of an oxidizing agent. Hydrogen peroxide is preferable as the oxidizing agent. This method does not require a step for purifying 2-amino-5-iodobenzoic acid or a step for recovering iodine, and 2-amino-5-iodobenzoic acid having excellent quality can be produced economically advantageously with a great yield. The product can be advantageously used as an intermediate for drugs, an agricultural chemical and a raw material for functional chemicals.

5 Claims, No Drawings

METHOD FOR PRODUCING 2-AMINO-5-IODOBENZOIC ACID

TECHNICAL FIELD

The present invention relates to a method for producing 2-amino-5-iodobenzoic acid by iodination of 2-aminobenzoic acid. 2-Amino-5-iodobenzoic acid is a compound useful as an intermediate compound for drugs, an agricultural chemical and a raw material for other functional chemicals.

BACKGROUND ART

2-Amino-5-iodobenzoic acid can be produced by iodination of 2-aminobenzoic acid, and a method in which 2-aminobenzoic acid is iodinated with iodine in an aqueous solution containing KOH is known (Non-Patent Reference 1). However, in accordance with this method, the yield of 2-amino-5-iodobenzoic acid of the object compound is as small as 72.2%. A half of iodine is recovered as KI without being used for the iodination of 2-aminobenzoic acid, and a step for recovering and recycling iodine is necessary. Therefore, the production process is complicated, and the production cost is great.

A method in which iodine chloride (ICl) is used as the iodinating agent is disclosed (Non-Patent Reference 2). However, crude crystals obtained after the iodination have a brown to purple color, and a step for purification is necessary. Therefore, it is described in Non-Patent Reference 2 that the obtained crude crystals are brought into reaction with a concentrated aqueous solution of ammonia in hot water to form an ammonium salt, the obtained ammonium salt is bleached with sodium hyposulfite, the bleached ammonium salt is then treated with decolorizing charcoal and subjected to acidolysis with hydrochloric acid, and 2-amino-5-iodobenzoic acid of the object compound is obtained with a yield of 76 to 84%. In accordance with this method, the ammonium salt obtained during the purification tends to be colored, and it is necessary that a great care be taken to prevent the coloring. As described above, the yield of 2-amino-5-iodobenzoic acid is small, and many complicated operations are necessary in the method disclosed in Non-Patent Reference 2.

As another route of synthesis of 2-amino-5-iodobenzoic acid, a method in which nitro group in 2-nitro-5-iodobenzoic acid is converted into amino group by reduction is reported (Non-Patent Reference 3). However, in this method, it is difficult that 2-nitro-5-iodobenzoic acid of the raw material is obtained industrially.

In Patent Reference 1, a method in which iodinated biphenyl is produced by bringing biphenyl and iodine or an iodide into reaction with each other in the presence of a solvent, hydrogen peroxide and sulfuric acid is described.

[Non-Patent Reference 1] Carl J. Klemme and James H. Hunter, J. Org. Chem., 5, 227-234, 1940

[Non-Patent Reference 2] V. H. Wallingfold and Paul A. Kruege, Org. Syn., Vol. 2, 349, 1943

[Non-Patent Reference 3] Otto Grothe, J. Prakt. Chem., <2>, 326, 1878

[Patent Reference] Japanese Patent Application Laid-Open No. Showa 63(1988)-91336

DISCLOSURE OF THE INVENTION

The present invention has been made to overcome the problems of the conventional methods described above and has an object of providing a method which does not require a step for purifying 2-amino-5-iodobenzoic acid or a step for recovering iodine and provides 2-amino-5-iodobenzoic acid having excellent quality economically advantageously with a great yield.

As the result of intensive studies by the present inventors to achieved the above object, it was found that iodine was consumed efficiently to the degree such that recovery of iodine was not necessary, the iodination could be conducted economically advantageously, and 2-amino-5-iodobenzoic acid having excellent quality could be obtained with a great yield when the iodination of 2-aminobenzoic acid was conducted in the liquid phase in the presence of an oxidizing agent such as hydrogen peroxide in the reaction system. The present invention was completed based on the knowledge.

The present invention provides a method for producing 2-amino-5-iodobenzoic acid by iodination of 2-aminobenzoic acid as described in the following:

(1) A method for producing 2-amino-5-iodobenzoic acid which comprises bringing 2-aminobenzoic acid (A) and molecular iodine (B) into reaction with each other in a liquid phase in a presence of an oxidizing agent.

(2) A method for producing 2-amino-5-iodobenzoic acid described in (1), wherein the oxidizing agent is hydrogen peroxide (C).

(3) A method for producing 2-amino-5-iodobenzoic acid described in (2), wherein a ratio of amounts by mole ([C]/[B]) of hydrogen peroxide (C) to molecular iodine (B) is in a range of 1 to 4.

(4) A method for producing 2-amino-5-iodobenzoic acid described in any one of (1) to (3), wherein acetic acid is used as a solvent.

THE MOST PREFERRED EMBODIMENT TO CARRY OUT THE INVENTION

In the present invention, 2-aminobenzoic acid (A) and molecular iodine (B) are brought into reaction with each other in the liquid phase. As the solvent used for the reaction, any solvent which can dissolve 2-aminobenzoic acid can be used, and it is preferable that acetic acid is used. When acetic acid is used as the solvent, acetic acid may be used alone or as a mixture with water. When acetic acid is used as a mixture, the content of acetic acid is not particularly limited as long as 2-aminobenzoic acid of the substrate is sufficiently dissolved. From this standpoint, it is preferable that the amount of water in the solvent is 4 parts by weight or smaller per 1 part by weight of acetic acid. It is preferable that the amount of acetic acid is in the range of 5 to 30 parts by weight per 1 part by weight of 2-aminobenzoic acid.

As the oxidizing agent, hydrogen peroxide (C) is preferable. In general, an aqueous solution of hydrogen peroxide is used. As the concentration of hydrogen peroxide, a great concentration exceeding 60% is not necessary, and a concentration in the range of 30 to 60% which is used industrially widely is suitable. The ratio of the amounts by mole ([C]/[B]) of hydrogen peroxide (C) to molecular iodine (B) is in the range of 1 to 4 and preferably in the range of 2 to 3. When the ratio of the amounts by mole is 1 or greater, the sufficient reaction rate and yield can be obtained. When the ratio of the amounts by mole is 4 or smaller, the decrease in the selectivity due to side reactions can be suppressed. When hydrogen peroxide is added, the entire amount of hydrogen peroxide may be added to the reaction system at the beginning of the reaction, or hydrogen peroxide may be added in portions while the reaction proceeds. From the standpoint of the efficiency of the reaction, it is preferable that hydrogen peroxide is added in portions while the reaction proceeds.

Hydrogen peroxide may used in combination with oxidizing agents other than hydrogen peroxide as long as the object of the present invention is not adversely affected. Examples of the oxidizing agent other than hydrogen peroxide include perchloric acid, perchloric acid salts such as sodium perchlorate and potassium perchlorate, periodic acid, periodic acid salts such as sodium periodate and potassium periodate and persulfuric acid salts such as sodium persulfate.

It is suitable that the amount of the molecular iodine (B) used in the present invention is in the range of 0.3 to 0.7 times by mole and preferably about 0.5 times by mole to the amount of 2-aminobenzoic acid. When the amount of the molecular iodine is such that the ratio of the amounts by mole ([B]/[A]) is 0.3 or greater, the productivity is improved since a great conversion can be obtained, and purification of the obtained 2-amino-5-iodobenzoic acid is not necessary since unreacted 2-aminobenzoic acid is not left remaining. When the amount of the molecular iodine is such that the ratio of the amounts by mole ([B]/[A]) is 0.7 or smaller, there is no possibility that products having higher boiling points are formed by diiodination due to further iodination of 2-amino-5-iodobenzoic acid of the object product. The entire amount of the molecular iodine may be added to the reaction system at the beginning of the reaction, or the molecular iodine may be added in portions while the reaction proceeds. It is not necessary that the molecular iodine is completely dissolved at the beginning of the reaction.

The temperature of the reaction can be selected in the range of the room temperature to the temperature of refluxing of the solvent (acetic acid) and is preferably in the range of the room temperature to 50° C. It is suitable that the time of the reaction is in the range of 1 to 5 hours although the time is different depending on the scale of the reaction and the temperature of the reaction.

In the method of the present invention, 2-amino-5-iodobenzoic acid having a great purity can be obtained with a great yield simply by separating the product by adding water to the reaction mixture after the iodination has been completed since the selectivity of 2-amino-5-iodobenzoic acid of the object product can be made great. It is suitable that the amount of water is, in general, in the range of 5 parts by weight or smaller per 1 part by weight of the reaction mixture although the amount is different depending on the concentration of the used substrate. The formed crystals can be recovered by filtration. It is possible that 2-amino-5-iodobenzoic acid thus obtained is recrystallized from acetic acid or methanol to further increase the purity of the obtained crystals.

EXAMPLES

The present invention will be described more specifically with reference to examples in the following. However, the present invention is not limited to the examples.

In the following, the conversion from 2-aminobenzoic acid of the raw material, the selectivity and the yield of 2-amino-5-iodobenzoic acid and the purity of 2-amino-5-iodobenzoic acid in the crystals were obtained by the analysis of the recovered crystals and the mother liquor or the reaction mixture in accordance with the high performance liquid chromatography.

In Table 1 showing the results in Examples and Comparative Examples, "5-iodo compound" means 2-amino-5-iodobenzoic acid, and "3-iodo compound" means 2-amino-3-iodobenzoic acid.

The yields of the isolated product mean the yields [(D/A), (D/2B)] of the object compound (2-amino-5-benzoic acid (D)) in the recovered crystals based on the amounts of 2-aminobenzoic acid (A) of the raw material and the iodine atom (the molecular iodine (B)×2), respectively.

Example 1

To a mixture of 5.00 g (36.4 mmole) of 2-aminobenzoic acid, 100 ml of acetic acid and 4.63 g (18.2 mmole) of molecular iodine, 2.06 ml (18.2 mmole) of a 30% by weight aqueous solution of hydrogen peroxide was added dropwise. After the reaction mixture was stirred at the room temperature (20° C.) for 5 hours, 360 ml of water was added, and 6.03 g of crystals were obtained by filtration. The results of the reaction (the conversion of 2-aminobenzoic acid, the selectivities of 2-amino-5-iodo-benzoic acid and 2-amino-3-iodobenzoic acid, the purity of 2-amino-5-iodobenzoic acid and the yields of isolated 2-amino-5-iodobenzoic acid) are shown in Table 1.

Example 2

To a mixture of 5.00 g (36.4 mmole) of 2-aminobenzoic acid, 100 ml of acetic acid and 4.63 g (18.2 mmole) of molecular iodine, 4.12 ml (36.4 mmole) of a 30% by weight aqueous solution of hydrogen peroxide was added dropwise. After the reaction mixture was stirred at the room temperature (20° C.) for 5 hours, the reaction mixture was added to 260 ml of water, and 7.57 g of crystals were obtained by filtration. The results of the reaction are shown in Table 1. The conversion increased by increasing the amount of hydrogen peroxide of the oxidizing agent.

Example 3

To a mixture of 5.00 g (36.4 mmole) of 2-aminobenzoic acid, 100 ml of acetic acid and 4.63 g (18.2 mmole) of molecular iodine, 4.12 ml (36.4 mmole) of a 30% by weight aqueous solution of hydrogen peroxide was added dropwise. After the reaction mixture was stirred at 50° C. for 3 hours, the reaction mixture was added to 400 ml of water, and 8.34 g of crystals were obtained by filtration. The results of the reaction are shown in Table 1.

Example 4

To a mixture of 20.00 g (145.6 mmole) of 2-aminobenzoic acid, 150 ml of acetic acid and 18.51 g (72.8 mmole) of molecular iodine, 16.53 ml (145.6 mmole) of a 30% by weight aqueous solution of hydrogen peroxide was added dropwise. After the reaction mixture was stirred at 50° C. for 1 hour, the reaction mixture was added to 200 ml of water, and 36.92 g of crystals were obtained by filtration. The results of the reaction are shown in Table 1.

Example 5

To a mixture of 5.00 g (36.4 mmole) of 2-aminobenzoic acid, 100 ml of acetic acid and 4.63 g (18.2 mmole) of molecular iodine, 8.24 ml (72.8 mmole) of a 30% by weight aqueous solution of hydrogen peroxide was added dropwise. After the reaction mixture was stirred at 50° C. for 1 hour, the reaction mixture was added to 400 ml of water, and 5.57 g of crystals were obtained by filtration. The results of the reaction are shown in Table 1. As described above, the yield of the isolated product decreased when the ratio of the amounts by mole ([C]/[B]) of hydrogen peroxide (C) to the molecular iodine (B) exceeded 4.

Example 6

To a mixture of 5.00 g (36.4 mmole) of 2-aminobenzoic acid, 100 ml of acetic acid and 4.63 g (18.2 mmole) of molecular iodine, 10.3 ml (91.0 mmole) of a 30% by weight aqueous solution of hydrogen peroxide was added dropwise. After the reaction mixture was stirred at the room temperature for 5 hour, the reaction mixture was analyzed in accordance with the high performance liquid chromatography. The results of the reaction are shown in Table 1. The selectivities of the object product decreased even at the low temperature when the ratio of the amounts by mole ([C]/[B]) of hydrogen peroxide (C) to the molecular iodine (B) was 5.0.

Example 7

To a mixture of 5.00 g (36.4 mmole) of 2-aminobenzoic acid, 100 ml of acetic acid and 4.63 g (18.2 mmole) of molecular iodine, 1.03 ml (9.1 mmole) of a 30% by weight aqueous solution of hydrogen peroxide was added dropwise. After the reaction mixture was stirred at the room temperature for 5 hour, the reaction mixture was analyzed in accordance with the high performance liquid chromatography. The results of the reaction are shown in Table 1. The conversion of 2-aminobenzoic acid markedly decreased when the ratio of the amounts by mole ([C]/[B]) of hydrogen peroxide (C) to the molecular iodine (B) was 0.5.

Example 8

To a mixture of 5.00 g (36.4 mmole) of 2-aminobenzoic acid, 100 ml of acetic acid and 3.56 g (14.0 mmole) of molecular iodine, 2.12 g (8.4 mmole) of a 70% by weight aqueous solution of iodic acid was added dropwise. After the reaction mixture was stirred at the room temperature for 3 hour, the reaction mixture was analyzed in accordance with the high performance liquid chromatography. The results of the reaction are shown in Table 1. It was shown by the values obtained by the analysis of the reaction mixture that the yield of 2-amino-5-iodobenzoic acid was 60% as calculated based on the amount of iodine atom (this result is shown in the parenthesis since this result is different from the yield of the isolated product). A relatively great conversion was obtained when iodic acid of the oxidizing agent was used as the iodinating agent. However, it was difficult that the selectivity of the object product as great as that obtained by using hydrogen peroxide was obtained.

Comparative Example 1

Into 63 ml of water containing 2.15 g (38.3 mmole) of KOH, 3.13 g (22.8 mmole) of 2-aminobenzoic acid was dissolved, and an alkaline solution prepared by dissolving 5.79 g (22.8 mmole) of molecular iodine in 32 ml of water containing 3.11 g (55.4 mmole) of KOH was added dropwise over 10 minutes. To the reaction mixture, 12.5 ml of acetic acid and 63 ml of water were added. The obtained mixture was stirred at the room temperature for 1 hour, and 4.78 g of crystals were obtained by filtration. The results are shown in Table 1. When KOH was used as the iodinating agent, a relatively great selectivity of 2-amino-5-iodobenzoic acid was obtained. However, as described in BACKGROUND ART, a half of iodine added into the reaction system was not used for the iodination but recovered as KI, and the step for recovering and recycling iodine was necessary. Therefore, the process was complicated, and the cost increased.

TABLE 1

| | Example | | | | | | | | Comparative Example |
|---|---|---|---|---|---|---|---|---|---|
| | 1 | 2 | 3 | 4 | 5 | 6 | 7 | 8 | 1 |
| Amount used (mmole) (raw material) | | | | | | | | | |
| 2-aminobenzoic acid (A) | 36.4 | 36.4 | 36.4 | 145.6 | 36.4 | 36.4 | 36.4 | 36.4 | 22.8 |
| molecular iodine (B) (oxidizing agent) | 18.2 | 18.2 | 18.2 | 72.8 | 18.2 | 18.2 | 18.2 | 14.0 | |
| hydrogen peroxide (C) | 18.2 | 36.4 | 36.4 | 145.6 | 72.8 | 91.0 | 9.1 | | |
| iodic acid | | | | | | | | 22.4 | |
| KOH | | | | | | | | | 55.4 |
| (ratio of amounts by mole) | | | | | | | | | |
| [B]/[A] | 0.5 | 0.5 | 0.5 | 0.5 | 0.5 | 0.5 | 0.5 | | 1.0 |
| [C]/[B] | 1.0 | 2.0 | 2.0 | 2.0 | 4.0 | 5.0 | 0.5 | | |
| Reaction temperature (° C.) | 20 | 20 | 50 | 50 | 50 | 20 | 20 | 20 | 20 |
| Reaction time (hour) | 5 | 5 | 3 | 1 | 1 | 5 | 5 | 3 | 1 |
| Results of reaction | | | | | | | | | |
| conversion (%) | 74.2 | 99.1 | 98.2 | 99.1 | 99.6 | 99.5 | 35.3 | 84.8 | 82.5 |
| selectivity | | | | | | | | | |
| 5-iodo compound (D) | 98.5 | 82.7 | 91.4 | 98.0 | 74.2 | 61.2 | 98.2 | 71.6 | 92.4 |
| 3-iodo compound | 1.5 | 1.7 | 2.4 | 2.0 | 1.6 | 1.2 | 1.2 | 2.1 | 2.3 |
| purity of crystals (%) | 98.9 | 98.7 | 98.1 | 98.4 | 99.6 | | | | 95.1 |
| yield of isolated product of object compound (D) (%) | | | | | | | | | |
| based on 2-aminobenzoic acid (A) | 62.1 | 77.9 | 85.3 | 94.7 | 56.5 | | | | 75.7 |
| based on iodine atom | 62.1 | 77.9 | 85.3 | 94.7 | 56.5 | | | [60] | 37.9 |

INDUSTRIAL APPLICABILITY

In accordance with the present invention, a step for purifying 2-amino-5-iodobenzoic acid or a step for recovering iodine is not necessary, and 2-amino-5-iodobenzoic acid having excellent quality can be produced economically advantageously with a great yield. The product can be advantageously used as an intermediate compound for drugs, an agricultural chemical and a raw material for functional chemicals.

The invention claimed is:

1. A method for producing 2-amino-5-iodobenzoic acid which comprises bringing 2-aminobenzoic acid (A) and molecular iodine (B) into reaction with each other in a liquid phase in a presence of an oxidizing agent, wherein the oxidizing agent is hydrogen peroxide (C).

2. A method for producing 2-amino-5-iodobenzoic acid according to claim 1, wherein a ratio of amounts by mole ([C]/[B]) of hydrogen peroxide (C) to molecular iodine (B) is in a range of 1 to 4.

3. A method for producing 2-amino-5-iodobenzoic acid according to claim 1, wherein acetic acid is used as a solvent.

4. A method for producing 2-amino-5-iodobenzoic acid according to claim 2, wherein acetic acid is used as a solvent.

5. A method for producing 2-amino-5-iodobenzoic acid which comprises bring 2-aminobenzoic acid (A) and molecular iodine (B) into reaction with each other in a liquid phase in a presence of an oxidizing agent, wherein acetic acid is used as a solvent.

* * * * *